(12) United States Patent
Xu et al.

(10) Patent No.: US 8,217,222 B2
(45) Date of Patent: Jul. 10, 2012

(54) METHODS FOR IDENTIFYING MARKERS FOR EARLY-STAGE HUMAN CANCER, CANCER PROGRESSION AND RECURRENCE

(75) Inventors: Mingxu Xu, San Diego, CA (US); Yuying Tan, San Diego, CA (US); Levy Kopelovich, Annandale, VA (US)

(73) Assignees: Anticancer, Inc., San Diego, CA (US); The United States of America as represented by the Department of Health and Human Services, Washington, DC (US)

( * ) Notice: Subject to any disclaimer, the term of this patent is extended or adjusted under 35 U.S.C. 154(b) by 607 days.

(21) Appl. No.: 11/529,938

(22) Filed: Sep. 29, 2006

(65) Prior Publication Data

US 2007/0196821 A1 Aug. 23, 2007

Related U.S. Application Data

(60) Provisional application No. 60/722,594, filed on Sep. 30, 2005.

(51) Int. Cl.
- *G01N 33/00* (2006.01)
- *A01K 67/00* (2006.01)
- *A01K 67/033* (2006.01)
- *C12N 5/00* (2006.01)
- *C12N 5/02* (2006.01)
- *C12N 15/00* (2006.01)
- *C12N 15/87* (2006.01)

(52) U.S. Cl. ............. 800/3; 800/10; 435/325; 435/455; 435/464

(58) Field of Classification Search ....................... 800/3
See application file for complete search history.

(56) References Cited

U.S. PATENT DOCUMENTS 5,922,601 A 7/1999 Baetscher et al.

FOREIGN PATENT DOCUMENTS

| EP | 1 279 730 | 1/2003 |
| WO | WO-98/49336 | 11/1998 |
| WO | WO-99/65928 | 12/1999 |
| WO | WO-01/85941 | 11/2001 |
| WO | WO-03/022863 | 3/2003 |

OTHER PUBLICATIONS

Diamandis, J. Natl. Cancer Inst. (2004) 96:353-356.
Fidler, Cancer Research (1978) 38:2651-2660.
Lai et al., PNAS USA (2002) 99:3651-3656.
Rai et al., Ann. NY Acad. Sci. (2004) 1022:286-294.
Albrethsen et al., BMC Cancer (2005) 5:8.
Fels et al., Digestive Diseases (2003) 21(4):292-298.
International Search Report and Written Opinion for PCT/US2006/038396, mailed on Apr. 27, 2007, 17 pages.
Levy et al., Bio/Technology (1996) 14(5):610-614.
Ferguson et al., Cancer Research (2005) 65(18):8209-8217.
Office Action for European Patent Application No. 06815994.6-1222, mailed Sep. 24, 2009, 6 pages.

*Primary Examiner* — Valarie Bertoglio
(74) *Attorney, Agent, or Firm* — Morrison & Foerster LLP

(57) ABSTRACT

A method is described to identify secreted proteins identified with stages of malignancy of cancer. The proteins are initially identified by trapping them with a fluorescent protein containing vector that can insert in any gene. The secreted proteins are initially identified by their fluorescence. Secreted proteins identifying tumors with specific degrees of malignancy are isolated to determine if they can serve as markers of cancer progression.

6 Claims, 2 Drawing Sheets

A. Vector Constructs

(i) Gene Trap Vectors

(ii) Control Vector

B. Helper Construct

C. Envelope Construct

METHODS FOR IDENTIFYING MARKERS FOR EARLY-STAGE HUMAN CANCER, CANCER PROGRESSION AND RECURRENCE

CROSS-REFERENCE TO RELATED APPLICATION

This application claims benefit of U.S. provisional application 60/722,594 filed Sep. 30, 2005. The contents of this document are incorporated herein by reference in their entirety.

TECHNICAL FIELD

The invention provides identification methods for secreted protein markers for cancer. Particularly, the invention uses gene-trap technology, which enables the detection of changes in gene expression.

BACKGROUND ART

The mortality from cancer mostly arises from late diagnosis at which time current therapeutics are ineffective. Although proteomics using mass spectrometry and other techniques enable characterization of proteins in serum, plasma, and urine, there is still a lack of useful early markers for the vast majority of cancer types (Rai et al., Ann. NY Acad. Sci. (2004) 1022:286-294; Diamandis, J. Natl. Cancer Inst. (2004) 96:353-356).

Historically candidate tumor markers were identified using monoclonal antibodies against tumor cell extracts (Fidler, Cancer Research (1978) 38:2651-2660). Screening and evaluation of these candidates has been the traditional method of identifying novel tumor markers. However, this technology has had limitations. It is labor intensive and time consuming to evaluate large numbers of candidate markers.

It has also been very difficult to identify markers that are sensitive and specific for a particular type of cancer. It is still difficult to identify markers for diagnosis, prognosis, staging, recurrence, and detection of minimal residual disease for most types of cancer.

SELDI-TOF mass spectrometry technology that is currently used for serum analysis is not capable of detecting any serum component at concentrations of less than 1 µg/mL (Lai et al., Proc. Natl. Acad. Sci. USA (2002) 99:3651:3656). This range of concentrations is approximately 1000-fold higher than the concentrations of known tumor markers in the circulation (Table 1) (Lai, supra):

TABLE 1

| Protein Classical tumor markers | Approx. concentration, pmol/L | Cancer type |
| --- | --- | --- |
| Alpha-fetoprotein | 150 | Hepatoma, testicular |
| Prostate-specific antigen | 140 | Prostate |
| Carcinoembryonic antigen | 30 | Colon, lung, breast |
| Human choriogonadotropin | 20 | Testicular, choriocarcinoma |
| Human choriogonadotropin-β subunit | 2 | Testicular, choriocarcinoma |

Reference: Diamandis, supra.

Gene-trap vectors mark endogenous genes and enable the detection of changes in gene expression. Marking a gene enables the study of a specific promoter and the function of the corresponding gene. However, gene-trap vectors, most of which are plasmid or retrovirus-based vectors, have been limited by low efficiency, short-term expression or restriction to dividing cells. Recently developed HIV-1-based lentiviral vectors have overcome these obstacles and are increasingly being used for gene delivery in vitro. These vectors have resulted in long term gene expression in vivo in cells of the central nervous system (CNS), hematopoietic system, retina, muscle, liver, and pancreatic islets (Lai, supra).

HIV-1 lentiviral vectors integrate into dividing and nondividing cell genomes and stably express the transgene. Two HIV-1-based lentiviral vector derivatives, pZR-1 and pZR-2, have been developed for gene-trapping in mammalian cells in vitro and in vivo (Lai, supra). These lentiviral gene-trap vectors contain a reporter gene, either β-lactamase or green fluorescent protein (GFP), that is inserted into the U3 region of the 3' long terminal repeat. Both of the trap vectors readily integrate into the host genome by using a convenient infection technique and result in GFP or β-lactamase expression. This technique facilitates rapid enrichment and cloning of the trapped cells. The reporter gene is driven by an upstream, cell-specific promoter (Lai, supra).

DISCLOSURE OF THE INVENTION

The inventive methods utilize gene-trap technology to identify secreted proteins that will serve as markers for various degrees of malignancy, such as early-stage human cancer, cancer progression and recurrence. In one representative embodiment, initially variants of malignant human cancer that have reverted toward the normal state (Jiang et al., Proc. Am. Assoc. for Cancer Res. (2004) 45:937) are transfected with the GFP-gene-trap vector described above. GFP-expressing cell lines are identified to determine if they secrete GFP-trapped-proteins. Clones of cells secreting GFP-linked proteins are implanted in mice to determine if GFP-linked proteins are secreted in serum. Such clones are evaluated in vivo to identify GFP-linked secreted proteins that are specific for the non-malignant variants. Subsequent experiments identify secreted GFP-linked variants that are specific for cancer progression using animals in which the non-malignant human variants re-revert back to various stages of malignancy. Parallel in vitro experiments are carried out on low malignancy human cell variants (Jiang, supra) in order to compare secreted GFP-linked proteins in vivo and in vitro in human cells that progress toward malignancy.

In one aspect, provided herein is a method to identify secreted protein markers for cancer comprising: a) transfecting a plurality of human cancer cells having varying degrees of malignancy and which have reverted toward a non-malignant state with an HIV-1 lentiviral-gene-trap vector containing a reporter gene; b) identifying reporter-expressing cell lines that secrete reporter-linked proteins in vitro; c) implanting a clone of each of the identified reporter-expressing cell lines in an animal; d) identifying an implanted reporter-expressing cell line clone which secretes a reporter-linked protein in serum; and e) identifying a secreted reporter-linked protein from step d) specific for human cancer cells of varying stages of malignancy from low to high; wherein the identified proteins are markers for each cancer stage. In one embodiment, the method further comprises f) identifying secreted reporter-linked proteins that are specific for cancer progression in which the non-malignant human cancer cells re-revert back to various stages of malignancy; wherein the identified proteins are markers for cancer progression and recurrence. The method can also further comprise g) comparing secreted reporter-linked proteins in low-malignancy human cancer cells in vitro and in vivo that progress toward malignancy.

In some embodiments, the reporter is GFP and step b) further comprises b1) transforming with RFP the transfected cancer cells reverted towards normal; b2) isolating and cloning GFP+ cells; b3) culturing GFP+ clones; b4) identifying GFP+ fluorescing clones; and b5) identifying cells which secrete GFP-proteins from the identified fluorescing clones.

The method can further comprise after step d), preparing a library of cells which cells secrete reporter- or GFP-proteins in vivo.

The reporter gene in the methods provided herein can be GFP or β-lactamase. The HIV-1 lentiviral gene-trap vector containing a reporter gene can an HIV-1 lentiviral-GFP-trap vector such as pZR-1 or pZR-2. The implanted clone can be selected from a prostate, testicular, lung, hepatoma, choriocarcinoma, breast, or colon cancer cell.

In another aspect, provided herein is a protein identified by the methods provided herein.

In yet another aspect, provided herein is a library comprising human cancer cells of varying degrees of malignancy, wherein said cells have randomly trapped genes, each containing a reporter gene. In some embodiments, the reporter gene expresses green fluorescent protein (GFP). It is contemplated that a subset of the human cancer cells cells contain reporter-trapped genes capable of encoding secreted proteins. In an embodiment, the reporter-trapped genes are capable of expressing proteins which are secreted in vitro. In some embodiments, the reporter-trapped genes are capable of expressing proteins which are secreted in vivo. The reporter-trapped genes can be capable of expressing proteins secreted in vitro or in vivo, when the cancer cells have a specific degree of malignancy. Sometimes, the cancer cells have a degree of malignancy such that the cells have the ability to invade or metastasize. In such cells, the reporter-trapped genes sometimes are capable of expressing proteins that are secreted in vitro and in vivo and are detectable in the serum of rodents transplanted with cells that express the reporter-trapped genes.

In one aspect, provided herein is a library of isolated genes which are capable of expressing protein markers of cancer progression identified by any of the methods disclosed herein, wherein the genes do not contain a reporter gene or a gene-trap vector during specific steps of tumor progression.

MODES FOR CARRYING OUT THE INVENTION

Figure 1:
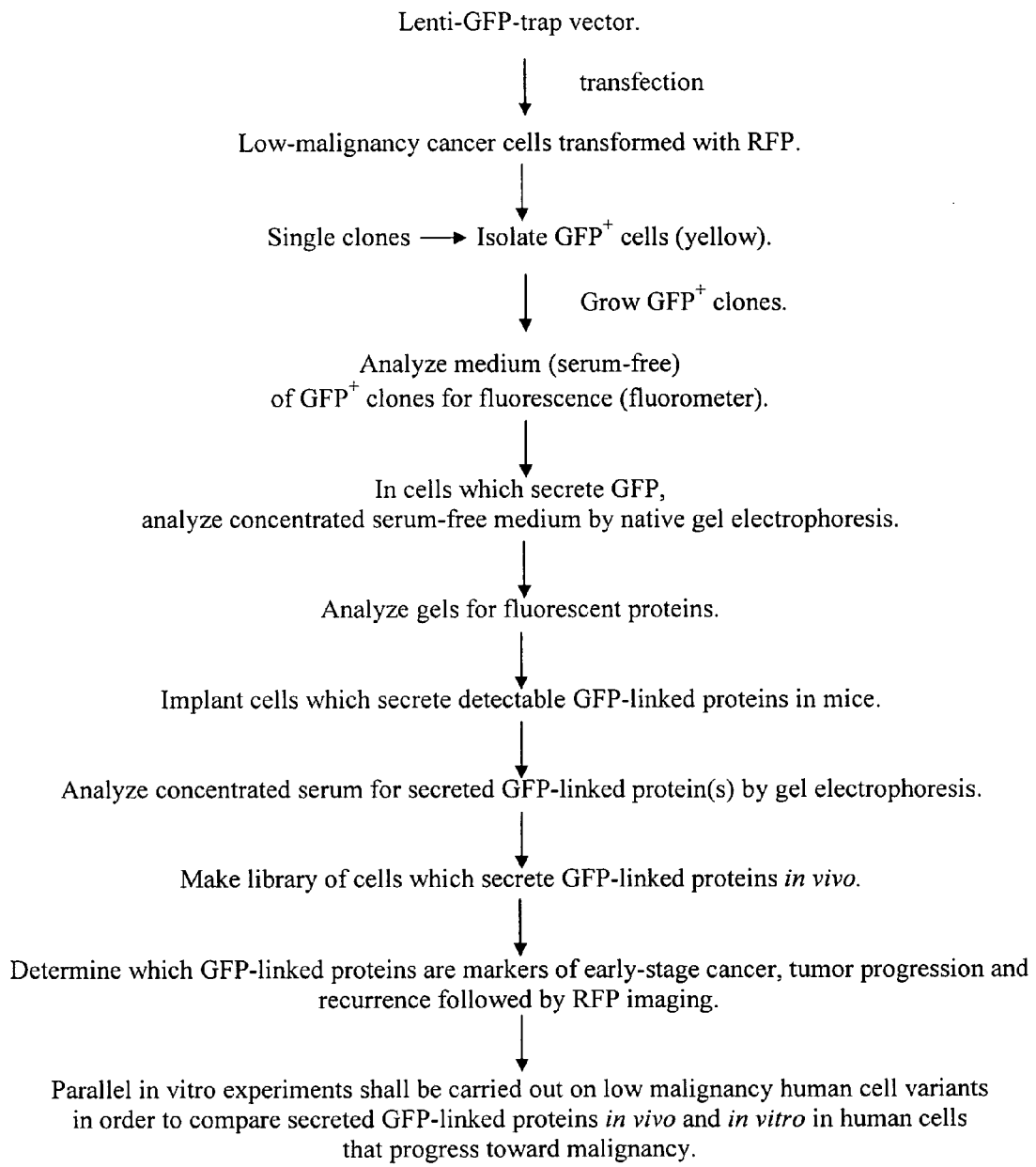
FIG. 1 is an experimental flow chart illustrating an embodiment of the invention.
Figure 2:
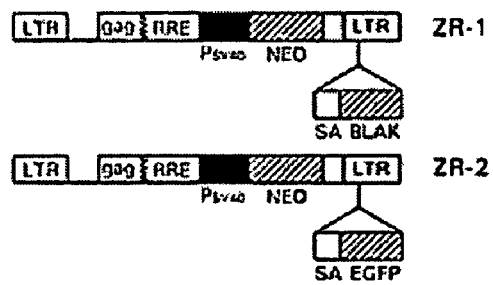
FIG. 2 depicts components of the HIV-1 lentiviral gene-trap vector system from Lai (supra). (A) Vector construct. (i) The gene-trap vectors contain a reporter gene, GFP (ZR-2) preceded by a splice acceptor site. (ii) An HIV-1 lentiviral control vector. BLAK, gene encoding β-lactamase; SA, Splice acceptor site. (B) Helper (Packaging) construct. (C) Envelope construct encoding vesicular stomatitis virus glycoprotein (VSV-G) (Lai, supra).
Figure 2:
Figure 2:
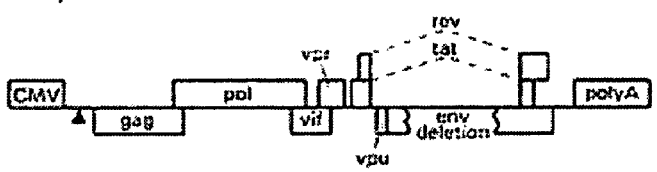
Figure 2:
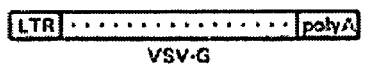

The invention methods take advantage of the HIV-1 lentiviral gene-trap vectors that contain a reporter gene, which is transfected into human cancer cells with varying degrees of malignancy. In one aspect, proteins are identified that are specific for human cancer cells that have reverted toward the normal state, and thus are considered "non-malignant" human cancer cells. As cells progress slightly from this state of non-malignancy toward malignancy, low-malignancy human cancer cells may be transfected. The non-malignant human cancer cells that re-revert back to various stages of malignancy are appropriate for identifying cancer progression and recurrence. Thus, the term "varying degrees of malignancy" refers to cancer cells which are in various stages of malignancy and/or non-malignancy.

A gene-trap vector of the invention preferably is an HIV-1 lentiviral gene-trap vector. Such a vector contains a reporter gene, such as green fluorescent protein (GFP) or β-lactamase. Other reporter genes may be used as well. The reporter gene may express another fluorophore, such as blue fluorescent protein (BFP) or a red fluorescent protein (RFP). Any method of operably linking the nucleotide sequence encoding the reporter to the lentiviral gene-trap vector falls within the scope of the invention. A reporter gene expressing GFP is preferred.

The method of the invention first involves an in vitro step. Reporter-expressing cell lines that secrete reporter-linked proteins are identified in vitro, thus in a serum-free medium. Cancer cells, preferably those reverted toward normal, which are expressing reporter-lentiviral vectors are cultured and analyzed for reporter expression, preferably GFP fluorescence. The cultures identified by the reporter are separated and grown. The medium from the reporter-linked protein-secreting cultures are concentrated, and then the components of the concentrated medium can be separated, such as by using native polyacrylamide gels, and are subjected to electrophoresis and fluorescence analysis to determine the position of the reporter-linked secreted proteins. The clones that secrete identifiable reporter-linked proteins are then further evaluated in vivo.

In vivo evaluation includes implanting in a laboratory animal such as in nude mice, cells identified as secreting reporter-linked proteins. Laboratory animals are typically rodents, such as mice, rats, or rabbits, but may also be other mammals such as monkeys. It is preferable that the reporter-linked proteins are secreted in a detectable amount, such that the cells are identifiable. The cells are grown in the animals and serum is collected and analyzed similarly to the way it is analyzed in vitro, as described above.

The invention also provides for analyzing the varying degrees of malignancy and progression of cells which secrete reporter-linked secreted proteins. Preferably, the cells are transformed with a reporter, preferably different from the reporter linked to the protein. For example, if the lentiviral gene-trap vector contains a GFP reporting gene, it would be beneficial if the cells were transformed with a different reporter gene, such as RFP. Cancer cells which are associated with reporter-linked secreted proteins can be allowed to re-revert back to their malignant state in vivo, and such a progression can be followed by observing the expression of a reporter gene different from that contained in the gene-trap vector. Serum samples, therefore, may be collected at different stages of tumor progression and analyzed for the presence of the reporter-linked secreted proteins using the methods described above. This data may be used to identify candidates of markers at specific stages of malignancy in vivo as well as continually in vitro, as the human cells re-revert to malignancy.

Example 1

Vector Construct and Virus Production

Plasmid NL-neo is based on the NL 4-3 molecular clone and carries a deletion from the NsiI site to the BglII site. A 1,169-bp fragment carrying the neo gene sequence and SV40 early promoter derived from pBKCMV (Stratagene) is inserted between the BamHI site and XhoI site. To construct the lentivirus-based gene-trap vectors, green fluorescent protein (GFP) is inserted into the U3 region of the 3' long terminal repeat (LTR) between the XhoI and XbaI sites to yield ZR-2 vectors (FIG. 1) (Lai, supra). A splice acceptor site is placed before the reporter gene to allow its expression from an upstream, cell-specific promoter.

To obtain valid translation of the fusion transcript, a polyadenylation signal in the gene cassette will stop transcription from the fusion gene (Lai, supra). The bacterial neo gene driven by an internal SV40 early promoter will be placed between the BamHI and XhoI sites in the lentiviral gene-trap vector, which allows for G418 selection (Lai, supra). Furthermore, pZR-2 is generated as a self-inactivating (SIN) lentiviral gene-trap vector in which the U3 region of the 3' LTR is deleted and replaced by the EGFP gene. Because the transcriptional inactivation of the long terminal repeat in the SIN provirus should prevent mobilization by replication-competent virus (Lai, supra), these modifications of the lentiviral gene-trap vectors should increase the safety of vector-mediated gene delivery and enhance transduction of genes into nondividing cells (Lai, supra).

For the preparation of HIV-1 pseudotypes, helper plasmid DNA (5 µg), Env plasma DNA (5 µg), and vector plasmid DNA (5 µg) are cotransfected into subconfluent 293 T cells by using a transfection kit (Stratagene) (Lai, supra). Approximately $2 \times 10^6$ cells per well are plated into a 6-well plate 24-30 h before transfection. The virus stocks are harvested 60-65 h after transfection and filtered through a 0.45-µm-pore-size filter, aliquoted, and frozen at −80° C. (Lai, supra).

Example 2

Human Tumor Cells with Varying Degrees of Malignancy

The various human clones shall be obtained as described (Jiang, supra).

Example 3

Transfection with Lenti-Viral-GFP Vector

Human tumor cells of varying degree of malignancy are transduced with lentiviral gene-trap vector ZR-2. Cells are grown on 12-mm round coverslips coated with poly-L-lysine (Becton Dickinson) in 12-well culture dishes in 2.2 ml of medium. For the generation of trapped cell lines, the cells are incubated with the lentiviral ZR gene-trap vector at 37° C. for 3-5 hours as described (Lai, supra). After G418 selection, drug-resistant colonies are transferred to a 24-well plate and expanded to confluence and observed under fluorescence microscopy for GFP-expression. Up to 100% cells transduced with the trap are GFP-positive, indicating that the transduction was highly efficient (Lai, supra).

Example 4

Orthotopic Implantation—Prostate

Mice are anaesthetized with a ketamine-xylazine-acepromazine maleate-cocktail and positioned supinely. An arc-shaped skin flap is made right above the pubis symphysis to expose the prostate gland. The fascia surrounding the prostate is carefully isolated and the two dorsal lateral lobes of the gland are exposed by a small incision using a pair of fine surgical scissors. Prostate cancer cells ($10^6$) expressing lenti-viral GFP are injected into one or both lobes. The abdomen is closed using a 6-0 suture. All procedures of the operation are performed with 7× dissection microscope.

Example 5

Orthotopic Implantation—Breast

Surgical orthotopic implantation is then performed as follows: Mice are anesthetized with a ketamine-xylazine-acepromazine maleate-cocktail and put in a supine position. The right second mammary gland is used for orthotopic implantation. A small incision is made along the medial side of the nipple. The mammary fat pad is exposed through blunt dissection. Cells expressing lenti-viral GFP are then injected. The skin is closed with a 6-0 silk suture. All procedures were carried out under a 5× dissecting microscope.

Example 6

Orthotopic Implantation—Colon

A small midline incision is made and colocecal part of the intestine is exteriorized. The serosa of the colon is removed and $10^6$ GFP-lentiviral-expressing tumor cells are injected. The intestine is returned to the abdominal cavity, and the abdominal wall is closed with 6-0 silk surgical suture.

Example 7

Fluorescence Microscopy

Light and fluorescence microscopy will be carried out with a Nikon microscope equipped with a xenon lamp power supply. A Leica stereo fluorescence dissecting microscope model LZ12 equipped with a mercury lamp power supply can also be used. Both microscopes have a GFP filter set (Chroma Technology, Brattleboro, Vt.). Photomicrographs are processed for brightness and contrast with Image Pro Plus Version 3.0 software (Media Cybernetics, Silver Spring, Md.).

Example 8

Fluorescence Imaging

For visualization of both GFP and RFP fluorescence simultaneously, excitation is produced through a D425/60 band pass filter and 470 DCXR dichroic mirror. Emitted fluorescence is collected through a long pass filter GG475 (Chroma Technology, Brattleboro, Vt.). Macroimaging is carried out in a light box (Lightools Research, Encinitas, Calif.). Fluorescence excitation of both GFP and RFP tumors is produced in the lightbox through an interference filter (440+/−20 nm) using slit fiber optics. Fluorescence is observed through a 520 nm long pass filter. Images from the microscope and light box are captured on a Hamamatsu C5810 3-chip cooled color CCR camera (Hamamatsu Photonics Systems, Bridgewater, N.J.).

Example 9

Identification of Secreted GFP-linked Proteins In Vitro

Clones of RFP-expressing cancer cells reverted toward normal (13) expressing GFP lentiviral vectors will be cultured in 24-well dishes. The conditioned medium from each well will be collected and initially analyzed for GFP fluorescence (excitation 490 nm/emission 510 nm) in a fluorometer. Those cultures with GFP fluorescence in the conditioned medium will then be grown in 6-well plates. The conditioned medium from these GFP linked protein-secreting cultures will be concentrated. The concentrated medium will then be applied on native polyacrylamide gels and subjected to electrophoresis. The gels will be photographed under fluorescent light to determine the position of GFP-linked secreted proteins. The clones that secrete identifiable GFP-linked proteins will then be further evaluated in vivo (please see below).

Example 10

Identification of GFP-linked Proteins Secreted In Vivo

Clones of RFP-expressing cancer cells reverted toward normal, identified to secrete specific GFP-linked proteins in vitro, as described above, will be implanted orthotopically in nude mice, as also described above. Serum from animals in which the implanted cells have been grown will be analyzed for GFP-linked proteins as described above. Cancer cells, from which GFP linked secreted proteins can be identified in serum, will be allowed to re-revert back to their malignant state in vivo as followed by RFP fluorescence. At various stages of tumor progression serum will be collected and analyzed for the presence of GFP-linked secreted proteins as described above. The totality of GFP-linked secreted proteins secreted from cells at varying degrees of malignancy and progression will be analyzed as candidates of markers of specific stages of malignancy in vivo as well as continually in vitro as the human cells re-revert to malignancy.

Example 11

Data Analysis

The statistical significance between the presence of a particular secreted GFP-linked protein and a malignant stage will be evaluated by the paired t-test with analysis of variance (ANOVA) where appropriate. Initial stages of malignancy will be defined as: 1) primary tumor less than 5 mm; 2) primary tumor less 1 cm; 3) presence of invasive local-regional cancer; 4) presence of distant metastasis. The cumulative data will be expressed as mean±SD with appropriate p values.

Example 12

Animals Used for Research

Approximately 500 athymic outbred nu/nu nude mice (male, age 5-6 weeks) will be used for the analysis of GFP-trapped secreted proteins from implanted cells of various degrees of malignancy.

Surgical Orthotopic Implantation (SOI)

Cells or tissue (1 mm$^3$), stably expressing GFP, previously grown subcutaneously in nude mice, are implanted by surgical orthotopic implantation (SOI) in nude mice. After proper exposure of the organ to be implanted, 8-0 surgical sutures are used to penetrate the tissue pieces and attach them on the appropriate orthotopic organ. The incision in the skin is closed with a 7-0 surgical suture in one layer. During surgery, a ketamine-xylazine-acepromazine maleate-cocktail will be utilized for anesthesia. All procedures of the operation described above are performed with a 7× magnification microscope (Leica MZ6, Nussloch, Germany). Finally, 50 µl suspension of $10^6$-$10^7$ cells is inserted in the host organ.

Skin Flap Window Models

Orthotopic GFP-expressing cells are visualized through skin flap windows over the upper abdominal wall. During surgery, a ketamine-xylazine-acepromazine maleate-cocktail will be utilized for anesthesia. Subcutaneous conjunctive tissue is separated to free the skin flap. The skin flap can be opened to expose the internal organs through the nearly transparent mouse body walls. This procedure not only allows reduce the depth of the organs to be imaged but also greatly reduce the scatter of green fluorescence. We have found that windows can be opened and closed three times a week without morbidity or infection with careful sterile surgery technique. The skin flap is treated with topical neosporin. Animals are kept in laminar flow racks in a barrier facility with ampicillin in the drinking water.

The invention claimed is:

1. A method to identify secreted protein markers for cancer progression which method comprises
   (a) implanting into a mammal cells of a cancer cell line that has been reverted to a non-malignant state, wherein said reverted cell line has been modified to contain:
      (i) a first fluorescent protein expressed in said cells and
      (ii) a gene-trap vector comprising a reporter that is a second fluorescent protein or β-lactamase;
   (b) monitoring the progression of said cancer by imaging the first fluorescent protein in said mammal; and
   (c) concomitantly detecting in serum from said mammal secreted amino acid sequences representing proteins coupled to the reporter; and
   (d) identifying as markers of progression proteins that correlate with the progression determined in (b).

2. The method of claim 1 wherein the gene-trap vector is an HIV-1 lentiviral-gene-trap vector.

3. The method of claim 2 wherein said HIV-1 lentiviral-gene-trap vector comprises a 5' long terminal repeat (LTR), a 3' LTR, a splice acceptor site (SA) at the 5' end of the reporter gene and a polyadenylation signal (polyA) at the 3' end of the gene, such that the SA-reporter gene-polyA cassette is inserted in the U3 region of the 3' LTR, and the SA facilitates expression of the reporter gene from an endogenous, cell-specific promoter.

4. The method of claim 1 wherein the first fluorescent protein is red fluorescent protein and the reporter is a second fluorescent protein which is green fluorescent protein (GFP).

5. The method of claim 1 which further includes performing parallel in vitro experiments wherein said non-malignant cell line is cultured concomitantly with monitoring the progression of said cancer and detecting secreted proteins from said cultured cell line coupled to the reporter.

6. The method of claim 1 wherein the mammal is a rodent.

* * * * *